United States Patent [19]

Hong

[11] 4,205,183
[45] May 27, 1980

[54] FACILE METHOD FOR ISOLATING RESOLVED AMINO ACIDS

[75] Inventor: Anita L. Hong, San Jose, Calif.

[73] Assignee: Beckman Instruments, Inc., Fullerton, Calif.

[21] Appl. No.: 967,747

[22] Filed: Dec. 8, 1978

[51] Int. Cl.$^2$ ............................................. C07B 19/02
[52] U.S. Cl. ..................................... 562/401; 435/280; 562/402
[58] Field of Search ..................... 562/401, 402; 195/2, 195/12, 30; 435/280

[56] References Cited

U.S. PATENT DOCUMENTS

| | | | |
|---|---|---|---|
| 2,511,867 | 6/1950 | Neuberg et al. | 435/280 |
| 3,813,317 | 5/1974 | Benoiton et al. | 435/280 |
| 3,979,457 | 9/1976 | Fujii et al. | 562/401 |

OTHER PUBLICATIONS

Yamada et al., *J. Agric. Food Chem.*, 23(4):653–657, (1975).

*Primary Examiner*—Bernard Helfin
*Assistant Examiner*—Vera C. Clarke
*Attorney, Agent, or Firm*—R. J. Steinmeyer; J. E. Vanderburgh; Robert S. Frieman

[57] ABSTRACT

A method for isolating D and L amino acids from a racemic mixture of the formula (DL)—H$_2$N—CHX—COOY, and salts thereof, wherein X denotes an amino acid side chain and derivatives thereof and Y denotes a suitable alkyl group. The racemic mixture is contacted with water to form an aqueous solution. This aqueous solution is then contacted with an esterase to thereby obtain a solution comprising the resolved amino acids (L)—H$_2$N—CHX—COOH and (D)—H$_2$N—CHX—COOY.

The N-terminus of the resolved (L) and (D) amino acids present in this solution are protected with an N-protecting group R to thereby obtain a solution comprising (L)—R—NH—CHX—COOH and (D)—R—NH—CHX—COOY.

The isolation of (L)—R—NH—CHX—COOH from (D)—R—NH—CHX—COOY is achieved in high yields by an acid-base extraction.

4 Claims, No Drawings

FACILE METHOD FOR ISOLATING RESOLVED AMINO ACIDS

BACKGROUND OF THE INVENTION

1. Field of the Invention

This invention relates to a method for isolating resolved amino acids.

2. Description of the Prior Art

In the prior art, the isolation of resolved amino acids is achieved by first hydrolyzing a racemic mixture having the formula (DL)—H$_2$N—CHX—COOY, with an esterase to yield a solution comprising (L)—H$_2$N—CHX—COOH and (D)—H$_2$N—CHX—COOY.

In order to isolate (L)—H$_2$N—CHX—COOH from this solution, several recrystallizations from water are required in the prior art. This recrystallization method is very laborious since (L)—H$_2$N—CHX—COOH and (D)—H$_2$N—CHX—COOY have almost the same solubilities in water. Therefore, utilizing tedious prior art recrystallization methods even highly skilled technicians can expect only marginal separation of the resolved amino acid moieties and low yields of (L)—H$_2$N—CH—COOH.

In addition, when the resolved amino acid (L)—H$_2$N—CHX—COOH is employed in a peptide synthesis, other than as the first C-terminal amino acid in a solution technique, one must always protect the N-terminus of the resolved amino acid with a suitable N-terminus protecting group. This step further reduces the amount of product obtained via the prior art process.

SUMMARY OF THE INVENTION

The instant invention encompasses a method for isolating resolved amino acids from a racemic mixture of the formula (DL)—H$_2$N—CHX—COOY, and salts thereof, wherein X denotes an amino acid side chain and derivatives thereof and Y denotes a suitable alkyl group.

In accordance with the invention separation of the D and L amino acids is readily accomplished with resultant improved yields. In addition, the separated D and L amino acids have their amino groups protected, thus making the separated amino acids ready for use in the preparation of peptide compositions.

The first step of the method of this invention comprises contacting the racemic mixture with water to form a solution. This solution is then contacted with an esterase to thereby obtain an aqueous solution comprising (L)—H$_2$N—CHX—COOH and (D)—H$_2$N—CHX—COOY. The N-terminus of the resolved (L) and (D) amino acids present in this aqueous solution is then protected with an N-protecting group, R, to obtain an aqueous solution comprising (L)—R—NH—CHX—COOH and (D)—R—NH—CHX—COOY. The aqueous solution is subsequently contacted with a suitable base capable of reacting with (L)—R—NH—CHX—COOH to form the N-protected, L-amino acid salt thereof. The aqueous solution is then contacted with a water immiscible organic solvent to form a water layer and an organic solvent layer whereby the N-protected, salt of (L)—R—NH—CHX—COOH is isolated in the water layer and whereby (D)—R—NH—CHX—COOY is isolated in the organic solvent layer. The water layer and organic solvent layer is separated into two fractions.

A suitable acid is added to the separated water fraction to neutralize the base present therein and obtain (L)—R—NH—CHX—COOH. The neutralized water fraction is then contacted with a suitable water immiscible organic solvent to form a second water layer and a second organic solvent layer whereby (L)—R—NH—CHX—COOH is isolated in the second organic layer. The second organic layer and second water layer are separated to thereby obtain a second water fraction and a second organic fraction.

The organic solvent is evaporated off from the separated second organic fraction layer to obtain (L)—R—NH—CHX—COOH.

(L)—R—NH—CHX—COOH can be employed in the synthesis of any desired peptide via any solid phase or solution technique known to those skilled in the art.

DESCRIPTION OF THE PREFERRED EMBODIMENTS

According to the invention, X can be any moiety that can be attached to the α-carbon atom of an amino acid. For example, X can be selected from a group consisting of CH$_3$—, (CH$_3$)$_2$CH—, (CH$_3$)$_2$CHCH$_3$—, (CH$_3$)(C$_2$H$_5$)CH—, —CH$_2$—CH$_2$—CH$_2$—, HOCH$_2$—, CH$_3$—CHOH—, HS—CH$_2$—, CH$_3$SCH$_2$CH$_2$—, HO$_2$C—CH$_2$—, HO$_2$C(CH$_2$)$_2$—, H$_2$NOC—CH$_2$—, H$_2$NOC—(CH$_2$)$_2$—, (NH$_2$)C(NH)—NH—(CH$_2$)$_3$—, H$_2$N—(CH$_2$)$_4$—,

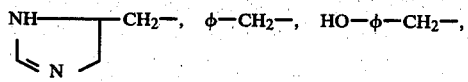, φ—CH$_2$—, HO—φ—CH$_2$—,

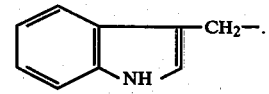.

In the method of the instant invention Y can be any alkyl group which does not sterically hinder the approach of the esterase and therefore interfere with the hydrolysis step. It is preferred that Y be an alkyl group containing from 1 to 5 carbon atoms.

Any esterase can be employed to hydrolyze the racemic mixture of amino acids in the instant invention. Examples of such esterases include α-chymotrypsin, cholinesterase, trypsin, and papain.

Similarly, any N-protecting group, R, can be employed in the method of the instant invention to protect the N-terminus of the resolved (L) and (D) amino acid moieties. Examples of said N-protecting groups are Boc-azide, Boc-Cl, t-butyl 2,4,5-trichlorophenyl carbonate, t-butyl-4,6-dimethylpyrimidine-2-yl-thiol carbonate, 2-t-butoxycarbonyloxyimino-2-phenyl-acetonitrile (Boc-ON), 1-methylcyclobutyloxycarbonyl (McBoc), cyclobutyloxycarbonyl (cBoc), 1-methylcyclohexyloxycarbonyl, cyclopropylmethyloxycarbonyl (cPoc), diphenylphosphenyl (Dpp), biphenyldimethylmethyl (Bpoc), t-butyloxycarbonyl (Boc), tertiary-amyl-oxycarbonyl (Aoc), and benzyloxycarbonyl (Z) groups.

The base employed in the process of the instant invention must be characterized by being capable of reacting with the N-protected amino acid, (L)—R—NH—CHX—COOH, to form its corresponding N-protected L-amino acid salt. Suitable bases meeting this criteria include triethylamine, dilute sodium carbonate, and dilute sodium bicarbonate. The dilute bases preferably have a concentration of from about 5 to about 10 percent by weight per unit volume (w/v).

The acid employed to neutralize the basic solution in the process of the instant invention must be capable of neutralizing the N-protected L-amino acid salt to form the N-protected amino acid, (L)—R—NHX—COOH, without removing the N-protecting group from the amino acid. Examples of acids which meet this criteria include dilute hydrochloric and dilute sulfuric acids. These acids preferably have a normality of from about 0.5 to about 1.5 N.

The water immiscible organic solvent employed in the instant invention must be capable of dissolving the L-R-amino acid, (L)—R—NH—COOH. Typical water immiscible solvents which can be used in the process of the instant invention include methylene chloride, chloroform, and ethyl acetate.

The following examples are provided for the purpose of further illustration only and are not intended to be limitations on the disclosed invention.

EXAMPLE 1

Prior Art Method For Isolating a Racemic Mixture of Resolved Amino Acids

To 5 gm of (DL)-p-Cl-Phe-OEt.HCl was added 80 ml water. Insoluble precipitates present in the solution were filtered out. The pH of the clear solution was adjusted to 5 via the addition of 0.1 M LiOH. To the solution was then added 300 mg of α-chymotrypsin. The pH of the solution was maintained constant at pH 5 by adding 0.1 M LiOH as required. After 2 hours another 50 mg of α-chymotrypsin was added. The reaction was completed after about 2.5 hours as shown by thin layer chromatography (TLC). The milky solution was filtered twice to remove the enzymes. The filtered solution was concentrated almost to dryness and again filtered. The crystals were washed with ethanol (EtOH). The washed crystals were then dissolved in 30 ml of hot water containing 5 ml of 0.1 N HCl and again filtered. To the filtrate was added 5 ml of 1 N LiOH. No crystals formed. Therefore, the solution was concentrated until crystals appeared. The crystals were washed with EtOH and then washed with ether. The resulting suspension was filtered. Difficulties were encountered during the filtration due to the tacking nature of the suspension's solid particles. Analysis of the solid particles by TLC showed less than 1% of the ether ester. The solid particles were washed with cold EtOH, dried with ether, and dried under a vacuum for about 16 hours. Yield was 0.76 grams of L-p-Cl-Phe or 40%.

L-p-Cl-Phe (1.1 gm; 0.0054 mole), as prepared above, was dissolved in a solution comprising 5 ml of 1 N HCl. To this solution was added sequentially 1.31 triethylamine (Et$_3$N) and 1.46 gm Boc-ON. This solution was stirred at room temperature for about 4 hours and then placed in a refrigerator for about 48 hours. (TLC of the reaction mixture after 4 hours showed that the reaction was completed at that time.) The solvent was evaporated off. Ether (30 ml) and 30 ml of water were then added to the residue. The ether layer was separated off and the aqueous layer was washed with more ether. TLC showed no Boc-p-Cl-Phe in the ether layer. The aqueous layer was acidified with 1 N HCl and extracted with CHCl$_3$. TLC analysis showed that all the Boc-p-Cl-Phe went into the CHCl$_3$ layer and none was present in the aqueous layer. The CHCl$_3$ was evaporated off. TLC with ninhydrin spray and iodine showed only one spot in a CMA (95 parts CHCl$_3$:5 parts MeOH:3 parts acetic acid) system.

Melting point: 107°–108° C.
Optical rotation: 20.06 [conc. 1.28, CH$_2$Cl$_2$].
Yield: 1.3 g or 80%.
Overall yield: 32%.

EXAMPLE 2

Method for Isolating a Racemic Mixture of Resolved Amino Acids Within Scope of Instant Invention To 5 gm of (DL)-p-Cl-Phe-OEt.HCl was added 80 ml of water and 300 mg of α-chymotrypsin as described in Example 1. After 2.5 hours the enzyme hydrolysis was completed. To the solution was added sequentially an aqueous solution comprising 15 ml water and 15 ml acetone; 1.5 ml Et$_3$N; and 5.98 gm of Boc-ON. The reaction was stirred for about 12 hours until TLC analysis showed only a negligible amount of p-Cl-Phe and p-Cl-Phe-OEt left. The acetone was then evaporated off. Ether was added and a small amount of p-Cl-Phe went into the ether layer but all the p-Cl-Phe-OEt went into the ether layer. TLC analysis showed that the p-Cl-Phe-OEt was absent from the water layer. The water layer was then acidified with 1 N HCl and extracted with CHCl$_3$. The p-Cl-Phe went into the CHCl$_3$ layer. The CHCl$_3$ layer was dried with Na$_2$SO$_4$ and then the CHCl$_3$ was evaporated off. TLC with ninhydrin spray and iodine showed only one spot in a CMA system.

Melting point: 107°–109° C.
Optical rotation: 19.7 [conc. 1.276, CH$_2$Cl$_2$].
Overall yield: 56%.

The overall yield obtained via the prior art process employed in Example 1 is 32%, whereas the overall yield obtained via a method within the scope of the instant invention as set forth in Example 2 is 56%. Therefore, in addition to having the advantage of employing a convenient procedure, the instant invention also enables one to obtain a yield approximately 1.75 times greater than the obtainable yield of the tedious procedure of the prior art.

The method of the instant invention can also be employed to isolate D and L amino acid moieties from a solution of resolved amino acid moieties comprising (L)—H$_2$N—CHX—COOH and (D)—H$_2$N—CHX—COOY irrespective of how the solution of resolved amino acids was formed.

Based on this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. A method for isolating L and D amino acids from a racemic mixture of the formula (DL)—H$_2$N—CHX—COOY, and salts thereof, wherein X is an amino acid side chain and derivatives thereof and wherein Y is a suitable alkyl group, comprising:
   (a) contacting said racemic mixture with water to form an aqueous solution;
   (b) contacting said aqueous solution with an esterase to thereby obtain an aqueous solution comprising the amino acids (L)—H$_2$N—CHX—COOH and (D)—H$_2$N—CHX—COOY;
   (c) protecting the N-terminus of the amino acids in said aqueous solution with a N-protecting group to thereby obtain an aqueous solution comprising (L)—R—NH—CHX—COOH and (D)—R—NH—CHX—COOY, wherein R represents said N-protecting group;

(d) contacting said aqueous solution with a base capable of reacting with (L)—R—NH—CHX—COOH to form the N-protected L-amino acid salt therof in said aqueous solution;

(e) contacting said aqueous solution with a suitable water immiscible organic solvent thereby forming a water layer and an organic solvent layer whereby said N-protected L-amino acid salt is isolated in said water layer and said (D)—R—NH—CHX—COOY is isolated in said organic solvent layer;

(f) separating said layers to thereby obtain a water fraction comprising said N-protected, L-amino acid salt and an organic fraction comprising said (D)—R—NH—CHX—COOY;

(g) adding a suitable acid to said water fraction to neutralize said base and thereby obtain (L)—R—NH—CHX—COOH;

(h) contacting said neutralized water fraction with a suitable water immiscible organic solvent thereby forming a second water layer and a second organic solvent layer whereby said (L)—R—NH—CHX—COOH is isolated in said second organic solvent layer;

(i) separating said second layers to thereby obtain a second organic fraction comprising said (L)—R—NH—CHX—COOH; and (j) evaporating off said organc solvent from said second organic fraction layer to obtain (L)—R—NH—CHX—COOH.

2. The method of claim 1 wherein X is selected from a group consisting of $CH_3$—, $(CH_3)_2CH$—, $(CH_3)_2CHCH_3$—, $(CH_3)(C_2H_5)CH$—, —$CH_2$—$CH_2$—$CH_2$—, $HOCH_2$—, $CH_3$—$CHOH$—, $HS$—$CH_2$—, $CH_3SCH_2CH_2$—, $HO_2C$—$CH_2$—, $HO_2C(CH_2)_2$—, $H_2NOC$—$CH_2$—, $H_2NOC$—$(CH_2)_2$—, $(NH_2)C(NH)$—$NH$—$(CH_2)_3$—, $H_2N$—$(CH_2)_4$—,

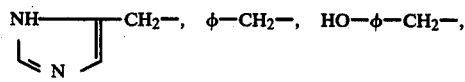

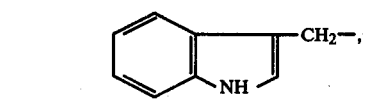

and derivatives thereof;

wherein Y is an alkyl group containing from 1 to 5 carbon atoms; wherein said esterase is selected from a group consisting of α-chymotrypsin, cholinesterase, trypsin, and papain;

wherein R is selected from a group consisting of Boc-azide, Boc-Cl, t-butyl 2,4,5-trichlorophenyl carbonate, t-butyl 4,6-dimethylpyrimidyl-2-thiol carbonate, and 2-t-butoxycarbonyloxyimino-2-phenyl-acetonitrile, 1-methylcyclobutyloxycarbonyl, cyclobutyloxycarbonyl, 1-methylcyclohexyloxycarbonyl, cyclopropylmethyloxycarbonyl, diphenylphosphenyl, biphenyldimethylmethyl, t-butyloxycarbonyl, tertiary-amyl-oxycarbonyl, and benzyloxycarbonyl groups;

wherein said base is selected from a group consisting of triethylamine and dilute $NaHCO_3$;

wherein said acid is selected from a group consisting of dilute hydrochloric and dilute sulfuric acids; and wherein said water immiscible solvent is selected from a group consisting of methylene chloride, chloroform, and ethyl acetate.

3. A method for isolating L and D amino acids from an aqueous solution of resolved amino acids comprising (L)—$H_2N$—CHX—COOH and (D)—$H_2N$—CHX—COOY, wherein X is an amino acid side chain and derivatives thereof and wherein Y is a suitable alkyl group, comprising:

(a) protecting the N-terminus of (L)—$H_2N$—CHX—COOH and (D)—$H_2N$—CHX—COOY present in said aqueous solution of resolved amino acids with an N-protecting group to thereby obtain an aqueous solution comprising (L)—R—NH—CHX—COOH and (D)—R—NH—CHX—COOY, wherein R represents said N-protecting group;

(b) contacting said aqueous solution with a base capable of reacting with (L)—R—NH—CHX—COOH to form the N-protected L-amino acid salt thereof in said aqueous solution;

(c) contacting said aqueous solution with a suitable water immiscible organic solvent thereby forming a water layer and an organic solvent layer whereby said N-protected L-amino acid salt is isolated in said water layer and said (D)—R—NH—CHX—COOY is isolated in said organic solvent layer;

(d) separating said layers to thereby obtain a water fraction comprising said L-amino acid salt and an organic fraction comprising said (D)—R—NH—CHX—COOY;

(e) adding a suitable acid to said water fraction to neutralize said base and thereby obtain (L)—R—NH—CHX—COOH;

(f) contacting said neutralized water fraction with a suitable water immiscible organic solvent thereby forming a second water layer and a second organic solvent layer whereby said (L)—R—NH—CHX—COOH is isolated in said second organic solvent layer;

(g) separating said second layers to thereby obtain a second organic fraction comprising said (L)—R—NH—CHX—COOH; and (h) evaporating off said organic solvent from said second organic fraction layer to obtain (L)—R—NH—CHX—COOH.

4. The method of claim 3 wherein X is selected from a group consisting of $CH_3$—, $(CH_3)_2CH$—, $(CH_3)_2CHCH_3$—, $(CH_3)(C_2H_5)CH$—, —$CH_2$—$CH_2$—$CH_2$—, $HOCH_2$—, $CH_3$—$CHOH$—, $HS$—$CH_2$—, $CH_3SCH_2CH_2$—, $HO_2C$—$CH_2$—, $HO_2C(CH_2)_2$—, $H_2NOC$—$CH_2$—, $H_2NOC$—$(CH_2)_2$—, $(NH_2)C(NH)$—$NH$—$(CH_2)_3$—, $H_2N$—$(CH_2)_4$—,

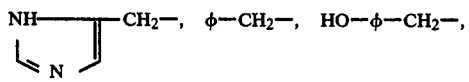

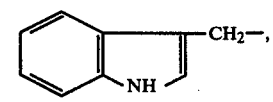

and derivatives thereof;

wherein Y is an alkyl group containing from 1 to 5 carbon atoms;

wherein R is selected from a group consisting of Boc-azide, Boc-Cl, t-butyl 2,4,5-trichlorophenyl carbonate, t-butyl 4,6-dimethylpyrimidyl-2-thiol carbonate, and 2-t-butoxycarbonyloxyimino-2-phenyl-acetonitrile, 1-methylcyclobutyloxycarbonyl, cyclobutyloxycarbonyl, 1-methylcyclohexyloxycarbonyl, cyclopropylmethyloxycarbonyl, diphenylphosphenyl, biphenyldimethylmethyl, t-butyloxycarbonyl, tertiary-amyl-oxycarbonyl, and benzyloxycarbonyl groups;

wherein said base is selected from a group consisting of triethylamine and dilute NaHCO$_3$;

wherein said acid is selected from a group consisting of dilute hydrochloric and dilute sulfuric acids;

and wherein said water immiscible solvent is selected from a group consisting of methylene chloride, chloroform, and ethyl acetate.

* * * * *